United States Patent
Romero et al.

(10) Patent No.: US 7,511,488 B2
(45) Date of Patent: Mar. 31, 2009

(54) VISCOSITY DETERMINATION FROM LOGARITHMIC MEAN RATIO OF RELAXATION TIMES

(75) Inventors: Pedro Antonio Romero, Buenos Aires (AR); Benito Eduardo Saavedra, Buenos Aires (AR); Hyung Tae Kwak, Spring, TX (US); Gabor Hursan, The Woodlands, TX (US)

(73) Assignee: Baker Hughes Incorporated, Houston, TX (US)

( * ) Notice: Subject to any disclaimer, the term of this patent is extended or adjusted under 35 U.S.C. 154(b) by 80 days.

(21) Appl. No.: 11/742,768

(22) Filed: May 1, 2007

(65) Prior Publication Data

US 2008/0272773 A1 Nov. 6, 2008

(51) Int. Cl.
*G01V 3/00* (2006.01)
(52) U.S. Cl. ....................................... 324/303
(58) Field of Classification Search ......... 324/300–322; 600/410–435
See application file for complete search history.

(56) References Cited

U.S. PATENT DOCUMENTS

| 4,710,713 | A |   | 12/1987 | Strikman |     |
|-----------|---|---|---------|----------|-----|
| 5,696,448 | A | * | 12/1997 | Coates et al. | 324/303 |
| 5,712,566 | A |   | 1/1998  | Taicher et al. |   |
| 6,084,408 | A | * | 7/2000  | Chen et al. | 324/303 |
| 6,229,308 | B1 | * | 5/2001 | Freedman | 324/303 |
| 6,765,380 | B2 | * | 7/2004 | Freedman et al. | 324/303 |
| 6,859,032 | B2 | * | 2/2005 | Heaton et al. | 324/303 |
| 6,859,033 | B2 | * | 2/2005 | Speier | 324/303 |
| 7,053,611 | B2 | * | 5/2006 | Freedman | 324/303 |

OTHER PUBLICATIONS

Seccombe, et al. "SPWLA Symposium Ranking Oil Viscosity in Heavy Oil Reservoirs". SPWLA 46th Annual Logging Symposium, Jun. 26-29, 2005. pp. 1-11.
Mullen, et al. "Fluid Typing with T1 NMR: Incorporating T1 and T2 Measurements for Improved Interpretation in Tight Gas Sands and Unconventional Reservoirs". SPWLA 46th Annual Logging Symposium, Jun. 26-29, 2005. pp. 1-13.
Hursan, et al. "New NMR Two-Dimensional Inversion of T1/T2APP vs. T2APP Method for Gas Well Petrophysical Interpretation". SPWLA 46th Annual Logging Symposium, Jun. 26-29, 2005. pp. 1-7.
Zhang, et al. "Oil and Gas NMR Properties: The Light and Heavy Ends". SPWLA 43rd Annual Logging Symposium, Jun. 2-5, 2002. pp. 1-2.

* cited by examiner

*Primary Examiner*—Dixomara Vargas
(74) *Attorney, Agent, or Firm*—Cantor Colburn LLP

(57) ABSTRACT

A method for determining viscosity, $\eta$, of a fluid downhole, calls for performing a nuclear magnetic resonance (NMR) survey of the fluid; determining a longitudinal relaxation time, $T_1$, and an apparent transverse relaxation time, $T_{2app}$, for the fluid; forming a ratio R of $T_1/T_{2app}$ for the fluid; and determining the viscosity, $\eta$, according to the ratio, R. A computer program product for implementing the method is provided.

18 Claims, 4 Drawing Sheets

-- PRIOR ART --

# VISCOSITY DETERMINATION FROM LOGARITHMIC MEAN RATIO OF RELAXATION TIMES

BACKGROUND OF THE INVENTION

1. Field of the Invention

This invention relates to assessments of borehole fluids, and in particular to determination of viscosity by use of nuclear magnetic resonance.

2. Description of the Related Art

Downhole characterization techniques are of considerable value for geophysical exploration. For example, characterization of parameters associated with downhole fluids provides for insight into quality of the fluid. More specifically, knowledge of viscosity, $\eta$, can provide insight into the quality of hydrocarbons in a formation. A number of technologies are applied downhole for various tasks. These technologies include nuclear magnetic resonance (NMR) imaging. Unfortunately, in the prior art, reliable use of NMR for determining viscosity, $\eta$, has not been realized.

Therefore, what is needed is a technique for estimating viscosity, $\eta$, of downhole fluids by use of NMR technologies.

BRIEF SUMMARY OF THE INVENTION

A method for determining viscosity, $\eta$, of a fluid downhole, the method calls for performing a nuclear magnetic resonance (NMR) survey of the fluid; determining a longitudinal relaxation time, $T_1$, and an apparent transverse relaxation time, $T_{2app}$, for the fluid; forming a ratio R of $T_1/T_{2app}$ for the fluid; and determining the viscosity, $\eta$, according to the ratio, R.

A computer program product stored on machine readable media and including machine readable instructions for determining viscosity, $\eta$, of a fluid downhole, the instructions including instructions for: performing a nuclear magnetic resonance (NMR) survey of the fluid; determining a longitudinal relaxation time, $T_1$, and an apparent transverse relaxation time, $T_{2app}$, for the fluid; forming a ratio R of $T_1/T_{2app}$ for the fluid; and determining the viscosity, $\eta$, according to the ratio, R.

BRIEF DESCRIPTION OF THE DRAWINGS

Referring now to the drawings wherein like elements are numbered alike in the several Figures.

DETAILED DESCRIPTION OF THE INVENTION

The teachings herein take advantage of various unique nuclear magnetic resonance (NMR) properties of materials to provide for determination of fluid viscosity downhole.

Figure 1:
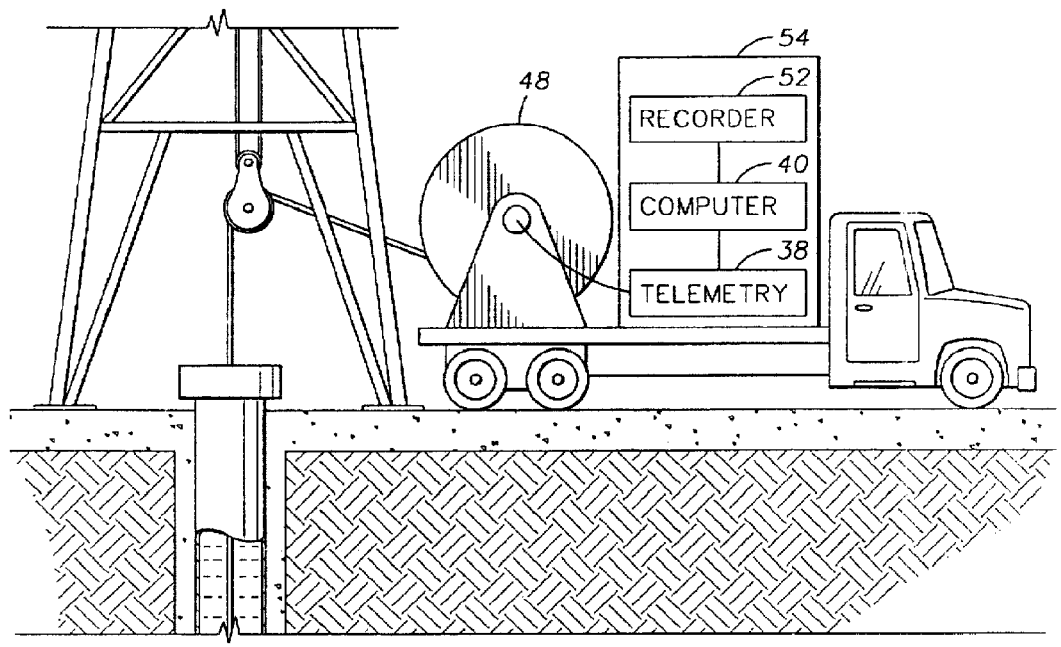
FIG. 1 depicts aspects of well logging with an nuclear magnetic resonance (NMR) apparatus.
Figure 1:
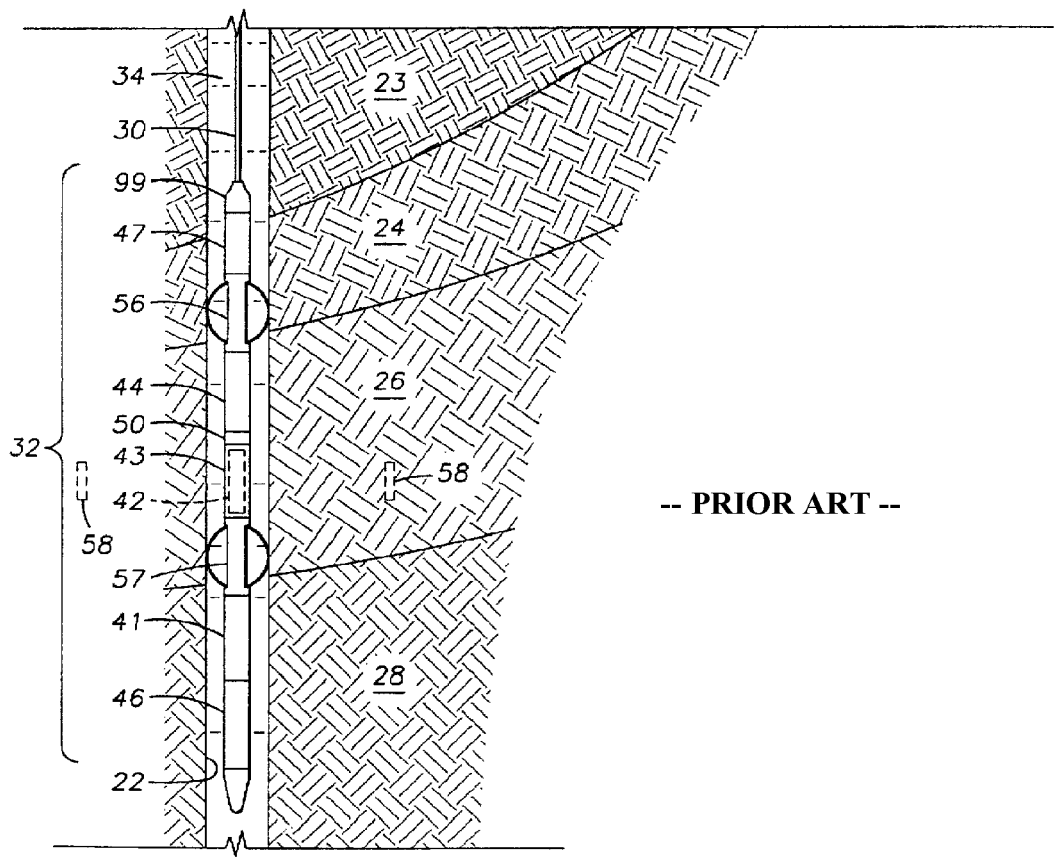

First, turn to FIG. 1 to consider aspects of downhole NMR characterizations, using a non-limiting embodiment of a wireline logging device. One skilled in the art will recognize that the techniques disclosed herein can be applied with other embodiments, such as logging-while-drilling (LWD) or measurements-while-drilling (MWD) operations.

FIG. 1 shows a well logging apparatus disposed in a wellbore 22 penetrating earth formations 23, 24, 26, 28 for making measurements of properties of the earth formations 23, 24, 26, 28 downhole. The wellbore 22 in FIG. 1 is typically filled with a fluid 34 known in the art as "drilling mud." A "sensitive volume," shown generally at 58 and having a generally cylindrical shape, is disposed in one of the earth formations, shown at 26. The sensitive volume 58 is a predetermined portion of the earth formations 26 in which nuclear magnetic resonance (NMR) measurements are made, as will be further explained or become apparent.

In typical embodiments, the sensitive volume 58 includes materials such as would be found downhole (below the surface and within or around the wellbore 22) including a mixture of liquids including gas, water, drilling fluid, oil and formation fluids that are indigenous to the formations 23, 24, 26, 28.

A string of logging tools 32, which can include an NMR apparatus, is typically lowered into the wellbore 22 by, for example, an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer may also include a data recorder 52 for recording measurements made by the apparatus and transmitted to the surface equipment 54. Typically, the computer includes a variety of input/output devices and other supporting devices to enhance the operation of the apparatus and estimations performed by use thereof. An NMR probe 42 can be included in the tool string 32.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other aspects of the exemplary embodiment of the NMR probe 42 are provided in U.S. Pat. No. 5,712,566, entitled "Nuclear Magnetic Resonance Apparatus and Method," issued Jan. 27, 1998 to Taicher et al., and incorporated herein by reference in it's entirety. Another non-limiting example is disclosed in U.S. Pat. No. 4,710,713, also issued to Taicher et al, and also incorporated by reference herein in it's entirety. It should be recognized that these embodiments of NMR tools are exemplary only, and not limiting of the teachings herein. A commercially available and exemplary embodiment of an NMR instrument is the MREX™, available from Baler Hughes, Incorporated of Houston Tex. Another exemplary instrument is the MAGTRAK™ instrument, also of Baker Hughes, Incorporated, which may be used for logging while drilling.

One skilled in the art will recognize that while the teachings herein may be performed downhole, they are also applicable to evaluations conducted on the surface, such as in a laboratory. Further, and as discussed elsewhere herein, at least a portion of an evaluation or determination may be performed in one place or another. For example, a property of a constituent may be determined in a laboratory, while other measurements and determinations are performed downhole.

As a matter of convention, one should note that the variables used herein appear throughout the disclosure. Accordingly, previously defined variables are generally not reintroduced. For convenience of referencing, some of the following representations are applied herein, or related to the teachings herein: $B_0$ represents static field strength; $B_1$ represents radiofrequency (RF) field strength; D represents diffusivity; f represents a two dimensional porosity distribution function; G represents RF field gradient strength; R represents a ratio of the longitudinal relaxation time, $T_1$, to the transverse relaxation time, $T_2$ (or $T_{2app}$, as the case may be); k represents a number of constituents (i.e., molecular types) within the mixture, and may be used as a subscript; M represents echo magnetization amplitude; where $M_z(t)$ represents a longitudinal magnetization, which involves a time constant $T_1$, where $T_1$ is the time required for the magnetization vector to be restored to 63% of its original amplitude (referred to as "longitudinal relaxation time"); $M_{x,y}$ represents a transverse magnetization, which involves a time constant $T_2$, where $T_2$ is the time required for the magnetization vector to drop to 37% of its original amplitude (referred to as "transverse relaxation time"); $T_{1,2}$ represents a combined relaxation time; $T_{2B}$ represents a bulk fluid transverse relaxation time; $T_{2cutoff}$ represents a dividing time; $T_{2diff}$ represents the characteristic decay time due to molecular diffusion in a magnetic field gradient environment; $T_{2app}$ represents an apparent transverse relaxation time; $T_{1,2bulk}$, which represents an addition of $T_{1,2inter}$ and $T_{1,2intra}$ where $T_{1,2inter}$ represents transverse and longitudinal relaxation time due to intermolecular interactions and $T_{1,2intra}$ represents transverse and longitudinal relaxation time due to intramolecular interactions; $T_{2surf}$ represents a surface relaxation time; $T_{1,LM}$ represents logarithmic mean longitudinal relaxation time; $T_{2,LM}$ represents logarithmic mean transverse relaxation time; $T_E$ represents an inter-echo time; $T_W$ represents a wait time; $t_k$ represents the time at the formation of the $k^{th}$ echo; v represent a frequency, and $\eta$ represents viscosity.

Figure 2:
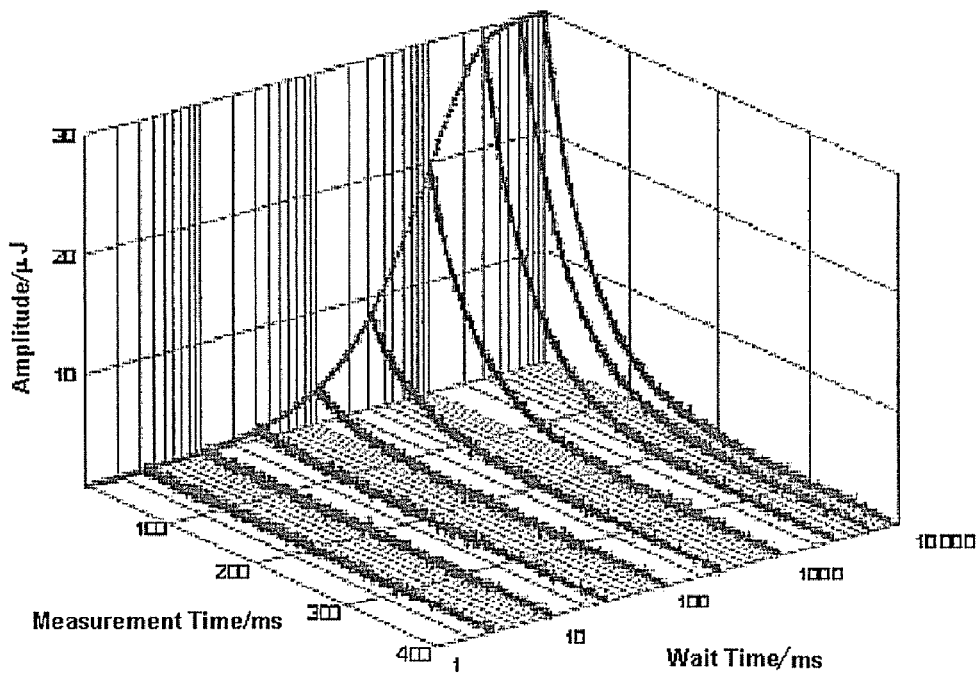
FIG. 2 depicts aspects of determinations of longitudinal relaxation time, $T_1$, by a series of measurements of transverse relaxation time, $T_2$, measurements during the polarization cycle.

The transverse relaxation time, $T_2$, is equal to, or shorter than the longitudinal relaxation time, $T_1$. This is mostly due to molecular diffusion within a gradient magnetic field because the transverse relaxation time, $T_2$, provides another relaxation mechanism. This mechanism acts in parallel with bulk and surface relaxation in the transverse plane. It is important to note that relaxation due to diffusion D only applies to the transverse relaxation time, $T_2$, and not to the longitudinal relaxation time, $T_1$, while bulk and surface relaxation are effective for both $T_1$ and $T_2$. As direct measurement of longitudinal magnetization is not feasible, determination requires tipping of the spins onto the transverse plane, as shown in FIG. 2. FIG. 2 depicts determination of $T_1$ by a series of $T_2$ measurements during a polarization cycle. Relaxation in the transverse plane is generally a more complex process as compared to $T_1$ relaxation.

The instrument using the NMR probe 42 is able to acquire multiple echo trains of diverse wait time $T_W$. Magnetization decay of the multiple echo trains, $M(t, T_W)$, can be represented by Eq. 1:

$$M(t,T_w) = \int \int f(T_{2app}, T_1)(1-e^{T_W/T_1})e^{-t/T_{2app}} dT_1 dT_{2pp} \qquad (1)$$

where M represents echo magnetization amplitude and f represents a two dimensional porosity distribution function. The two-dimensional (2D) term here represents the two dimensions in the parameter domain, $T_1$ and $T_{2app}$. A polarization factor, $1-e^{-T_W/T_1}$, is important for analyzing the data because different fluid types have different $T_1$. The echo decay factor, $e^{-t/2app}$, where $T_{2app}$ represents the apparent transverse relaxation time and t represents a duration of the echo train, is not only determined by the fluid properties but also is controllable by the acquisition parameters g and $T_E$, as provided in Eq. (2):

$$\frac{1}{T_{2app}} = \frac{1}{T_{2,i}} + \frac{(\gamma * g * T_E) * D}{12}. \qquad (2)$$

In general, Eq. (1) may be inverted to obtain both the relaxation time distributions for $T_1$ and $T_{2app}$. Alternatively, Eq. (1) can be reformulated by substituting Eqs. (3) to provide for Eq. (4):

$$T_1 = R * T_{2app} \qquad (3)$$

$$E(t,T_w) = \int \int g(T_{2app},R)(1-e^{T_w/R*T_{2app}})e^{-t/T_{2app}} dR\, dT_{2app} \qquad (4);$$

where R represents a ratio of $T_1/T_{2app}$. This provides for solving for a two-dimensional parameter distribution function $g(T_{2app}, R)$. By doing this substitution, differences related to the ratio R may be observed on a 2D map.

Experimentation has shown that, for at least some conditions, a correlation between the ratio, R, and the viscosity, $\eta$, exists. For example, as the oil viscosity increases over about 100 cp, for a magnetic field frequency of about two (2) MHz, the ratio R may differ from one (1).

One skilled in the art will recognize that a variety of aspects and parameters used in an NMR survey may be modified for use of certain algorithms. The foregoing is merely one non-limiting example of setting bounds or ranges for obtaining desired data.

By determining the ratio of $T_1$ over $T_{2app}$ (R) from an inversion algorithm such as the one provided above (with reference to Eqs. 1-4), it is possible to identify aspects of the viscosity, $\eta$. For example, heavy oil may be identified. A ratio of $T_1/T_{2app}$ that is close to one (1), frequently corresponds to light oil with low gas-to-oil ratio (GOR), while a higher result will typically correspond to heavy oil. In short, the ratio R typically increases with increasing viscosity, $\eta$. In other embodiments, light oils with a significant GOR may exhibit a high ratio, R, in contrast to the behavior of heavy oils having a lower viscosity, $\eta$ and higher ratio, R. In general a plot of the ratio, R, versus the viscosity, $\Theta$, has a V-shaped form, with varying slope between light oil and heavy oil.

In other embodiments, determination of the relaxation time ratio, R, is useful for determining viscosity, $\eta$, of foamy oil. For example, foamy heavy oil, typically exhibits a higher $T_1/T_{2app}$ ratio R than non-foamy heavy oil. This is usually a consequence of gas in solution with the oil. The foamy oil maybe more affected by the field gradient than the non-foamy oil, thus reducing the associated $T_{2app}$.

Figure 3:
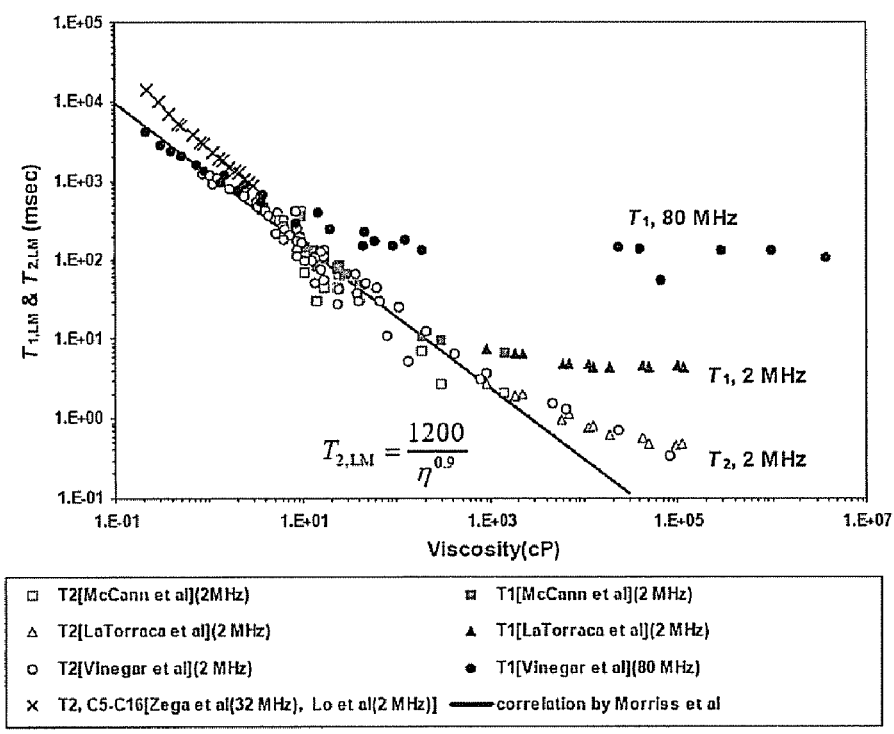
FIG. 3 depicts $T_1$ and $T_2$ relaxation times for measurement standards for alkanes, crude oils, and viscosity.
Figure 4:
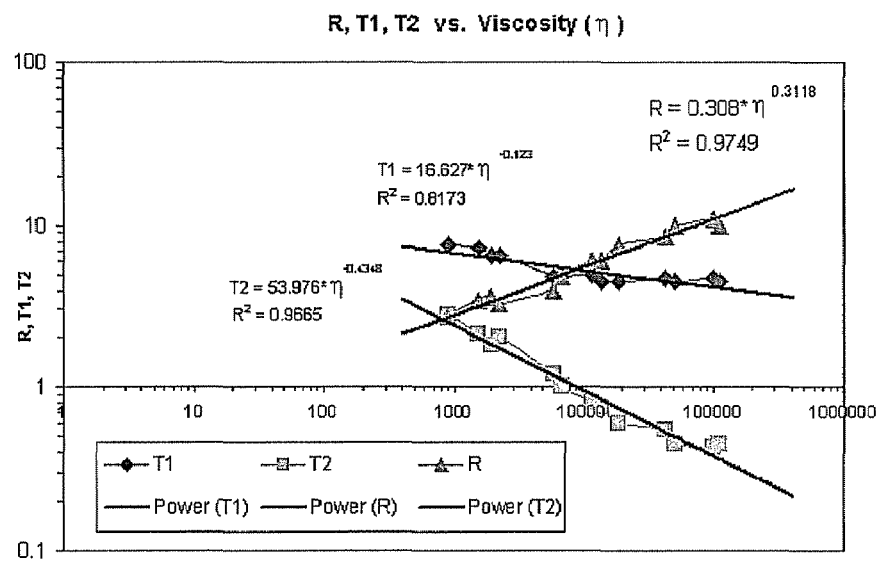
FIG. 4 depicts power functions relating $T_1$ and $T_2$ relaxation times and a ratio R with viscosity.

As one skilled in the art would expect, in cases of light oil with a significant GOR ratio, the $T_1/T_{2app}$ increases. Exemplary relationships of the ratio R and viscosity, $\eta$, are depicted in FIGS. 3 and 4. FIG. 3 depicts relaxation times for certain standards, wherein measurements were completed using a Larmor frequency of between about 2 MHz and 80 MHz. In other embodiments, the frequency is between about 0.5 MHz and about 100 MHz. FIG. 4 depicts power fits to data sets of the relaxation times $T_1$ and $T_2$, as well as the ratio R. In other embodiments, fits other than power functions may be applicable. For example, an exponential function may be relevant. In some embodiments, an exponential function is developed as a series of power functions using a Taylor series approach.

It should be noted that typically, heavy oil exhibits a distribution for the transverse relaxation time $T_2$ that is in a range of below about 33 milliseconds (ms) down to about 1 ms, and may be even shorter (as in the case of extra heavy oil). The distribution for the longitudinal relaxation time, $T_1$, however, may show values up to an order of magnitude higher than the transverse relaxation time $T_2$. Integration of geochemical data and the NMR results indicate a strong correlation between $T_{1,LM}$ (a logarithmic mean of the $T_1$) and viscosity, $\eta$. It is recognized that the techniques disclosed herein do reach certain limitations. However, in general, as far as an oil can be measured with using NMR, the ratio R may be related to the viscosity, $\eta$.

Figure 5:
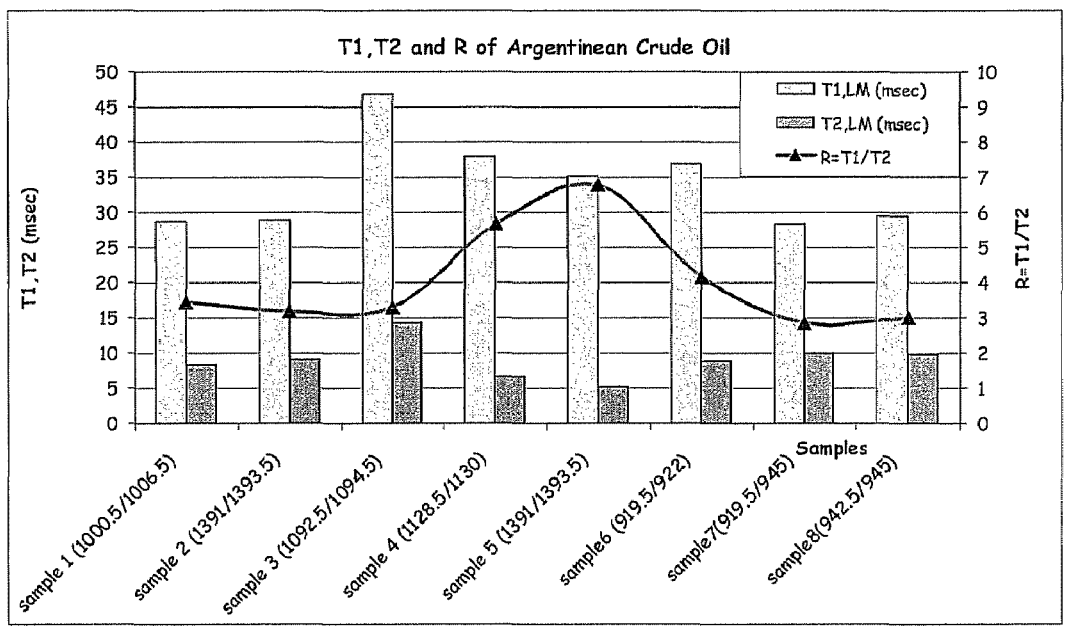
FIG. 5 is a bar chart showing variation in a logarithmic mean for longitudinal relaxation time $T_{1,LM}$ and transverse relaxation time $T_{2,LM}$ and the ratio R for various fluid samples.
Figure 6:
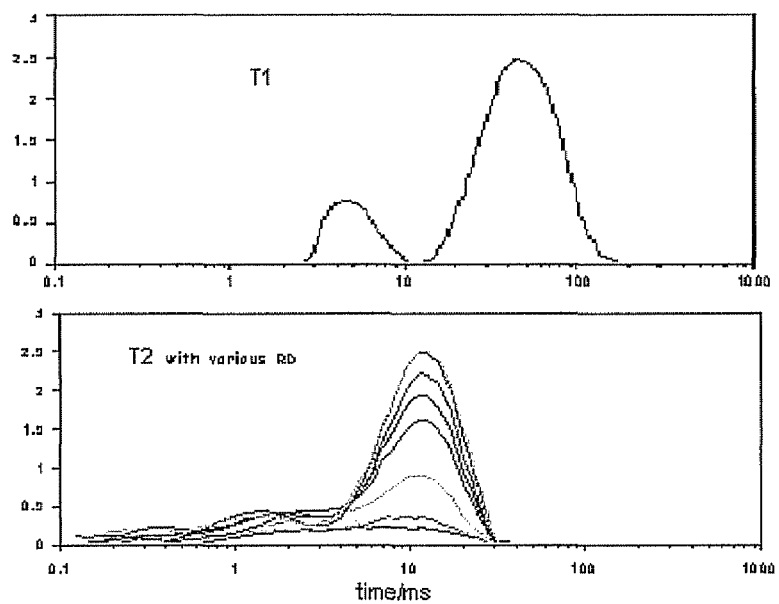
FIG. 6 depicts results of lab measurements for $T_1$ and $T_2$ using with different recycling delays (t) for Sample 5 of FIG. 5.
Figure 7:
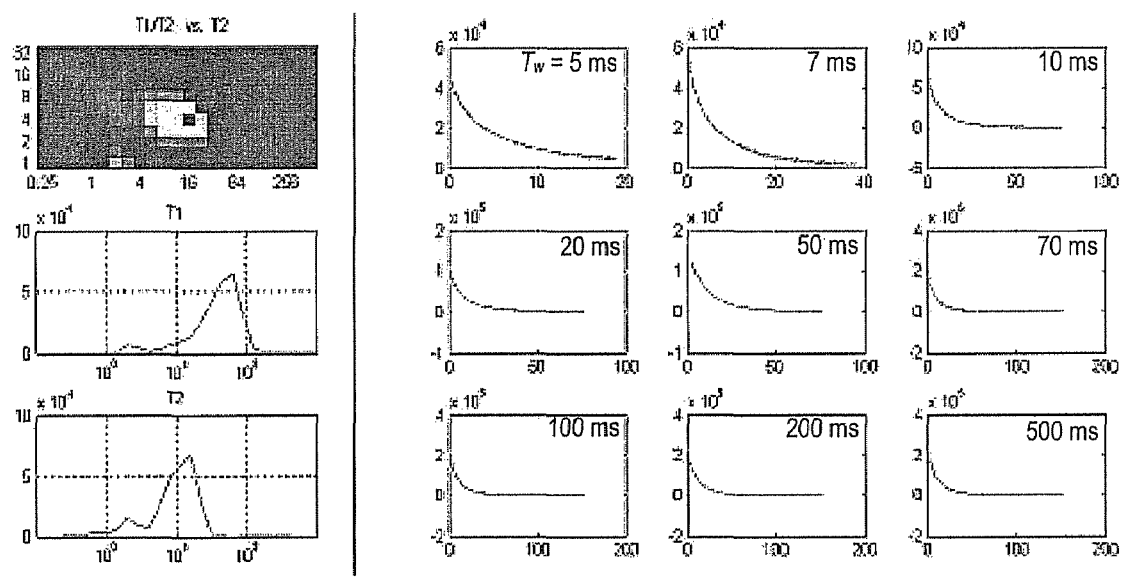
FIG. 7 depicts graphs of the ratio R for various echo trains.

In FIG. 5, relationships between the ratio, R, and logarithmic mean (LM) for $T_1$ and $T_2$ are depicted for various samples. These samples were each taken from the San Jorge Basin in Argentina. Further aspects of the samples presented in FIG. 5 are shown in the FIG. 6. From the various samples, the No. 5 sample was selected for calculating the ratio, R, using the technique described above with reference to Eqs. (1-4). The distribution for $T_1$ and the different distributions for $T_2$ are shown in FIG. 5. The various $T_2$ distributions are shown wait times, $T_W$, of 5 milliseconds (ms), 7 ms, 10 ms, 20 ms, 50 ms, 70 ms, 100 ms, 200 ms and 500 ms. FIG. 7 shows results of the inversion for R, as well as the calculated distributions for $T_1$ and $T_2$ according to the wait time, $T_w$. These results correlate quite well with the measurement shown in FIG. 6, and the set of echo trains used for the inversion.

It is noted that the term "recycling delay (RD)" is equivalent to the wait time $T_w$, and that the terminology selected for use generally depends on modeling software (such as Maran software and MRLAB software). In other embodiments, the wait time, $T_w$, is between about 5 ms and 10,000 ms.

The foregoing procedure is also valid when diffusivity, D, is very low or the magnetic field gradient, G, is low or zero, so that $T_{2app}$ is near or equal to $T_{2intrinsic}$ (from intra and inter molecular nature). In some embodiments, the procedure calls for replacing peak values with a logarithmic mean combined relaxation time, $T_{1,2}$, when a combined relaxation time distribution exhibits one of a sharp appearance and a Gaussian shape.

In support of the teachings herein, various analysis components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining viscosity, $\eta$, of a fluid downhole, the method comprising:
   performing a nuclear magnetic resonance (NMR) survey of the fluid;
   determining a longitudinal relaxation time, $T_1$, and an apparent transverse relaxation time, $T_{2app}$, for the fluid wherein obtaining a magnetization decay of multiple NMR echo trains provides for determining $T_1$ and $T_{2app}$;
   forming a ratio R of $T_1/T_{2app}$ for the fluid;
   determining the viscosity, $\eta$, according to the ratio, R; and
   providing the viscosity to a user as a result.

2. The method as in claim 1, wherein $T_{2app}$ is approximately equal to an intrinsic transverse relaxation time, $T_{2intrinsic}$, when a radiofrequency field gradient strength, G, is about equal to zero.

3. The method as in claim 1, wherein determining $T_1$ and $T_{2app}$ comprises solving the relationship:

$$M(t,T_w) = \int\int f(T_{2app}, T_1)(1-e^{T_w/T_1})e^{-t/T_{2app}} dT_1 dT_{2pp}$$

where
   $T_w$ represents a wait time;
   t represents a duration of an echo train; and
   f represents a two dimensional porosity distribution function.

4. The method as in claim 3, wherein the following relationship is substituted for the longitudinal relaxation time, $T_1$:

$$T_1 = R*T_{2app}.$$

5. The method as in claim 4, wherein the substitution provides the relationship:

$$E(t,T_w) = \int\int g(T_{2app},R)(1-e^{T_w/R*T_{2app}})e^{-t/T_{2app}} dR\, dT_{2app} dR\, dT_{2app}$$

where g represents an acquisition parameter.

6. The method as in claim 1, wherein the survey is performed using a magnetic field frequency of about 0.5 MHz to about 100 MHz.

7. The method as in claim 1, wherein the wait time, $T_W$, is between about 5 milliseconds (ms) and about 10,000 ms.

8. The method as in claim 1, wherein forming a ratio R comprises determining a logarithmic mean for at least one of the transverse relaxation time, $T_2$, and the longitudinal relaxation time, $T_1$.

9. The method as in claim 1, further comprising replacing peak values with a logarithmic mean combined relaxation time, $T_{1,2}$, when a combined relaxation time distribution exhibits one of a sharp appearance and a Gaussian shape.

10. The method as in claim 1, wherein the viscosity, $\eta$, is related to at least one of the transverse relaxation time, $T_2$, the longitudinal relaxation time, $T_1$, and the ratio, R, by one of a power function, an exponential function and a Taylor series.

11. A computer program product stored on machine readable media comprising instructions for determining viscosity, $\eta$, of a fluid downhole, the instructions comprising instructions for:
performing a nuclear magnetic resonance (NMR) survey of the fluid;
determining a longitudinal relaxation time, $T_1$, and an apparent transverse relaxation time, $T_{2app}$, for the fluid;
forming a ratio R of $T_1/T_{2app}$ for the fluid; and p1 determining the viscosity, $\eta$, according to the ratio, R; and providing the viscosity to a user as a result;
wherein a wait time, $T_w$, is between about 5 milliseconds (ms) and about 10,000 ms.

12. The computer program product as in claim 11, wherein obtaining a magnetization decay of multiple NMR echo trains provides for determining $T_1$ and $T_{2app}$.

13. The computer program product as in claim 12, wherein determining $T_1$ and $T_{2app}$ comprises solving the relationship:

$$M(t,T_w)=\int\int f(T_{2app},T_1)(1-e^{T_w/T_1})e^{-t/T_{2app}}dT_1 dT_{2pp}$$

where $T_w$ represents a wait time;

t represents a duration of an echo train; and f represents a two dimensional porosity distribution function.

14. The computer program product as in claim 13, wherein the following relationship is substituted for the longitudinal relaxation time, $T_1$:

$$T_1=R*T_{2app}.$$

15. The computer program product as in claim 14, wherein the substitution provides the relationship:

$$E(t,T_w)=\int\int g(T_{2app},R)(1-e^{T_w/R*T_{2app}})e^{-t/T_{2app}}dR\,dT_{2app}R$$

where g represents an acquisition parameter.

16. The computer program product as in claim 11, wherein the survey is performed using a magnetic field frequency of about 0.5 MHz to about 100 MHz.

17. The computer program product as in claim 11, wherein forming a ratio R comprises determining a logarithmic mean for at least one of the transverse relaxation time, $T_2$, and the longitudinal relaxation time, $T_1$.

18. The computer program product as in claim 11, wherein the viscosity, $\eta$, is related to at least one of the transverse relaxation time, $T_2$, the longitudinal relaxation time, $T_1$, and the ratio, R, by one of a power function, an exponential function and a Taylor series.

* * * * *